United States Patent
Villa et al.

(10) Patent No.: US 6,448,408 B1
(45) Date of Patent: Sep. 10, 2002

(54) PROCESS FOR THE PREPARATION OF HETEROARYL-PHENYLALANINES

(75) Inventors: Marco Villa, Milan (IT); Maurizio Paiocchi, Milan (IT); Katiuscia Arrighi, Cabiate (IT)

(73) Assignee: Zambon Group S.p.A., Vicenza (IT)

( * ) Notice: Subject to any disclaimer, the term of this patent is extended or adjusted under 35 U.S.C. 154(b) by 0 days.

(21) Appl. No.: 09/331,164

(22) PCT Filed: Dec. 15, 1997

(86) PCT No.: PCT/EP97/07024

§ 371 (c)(1),
(2), (4) Date: Jun. 21, 1999

(87) PCT Pub. No.: WO98/28284

PCT Pub. Date: Jul. 2, 1998

(30) Foreign Application Priority Data

Dec. 24, 1996 (IT) .......................................... MI96A2738

(51) Int. Cl.⁷ ............................................. C07D 277/30
(52) U.S. Cl. ....................................................... 548/205
(58) Field of Search ......................................... 548/205

(56) References Cited

FOREIGN PATENT DOCUMENTS

WO 97 24342 7/1997

OTHER PUBLICATIONS

Mark J. Burk et al., "A versatile tandem catalysis procedure for the preparation of novel amino acids and peptides" *Journal of the American Chemical Socitey*, vol. 116, No. 23, 1994, pp. 10847–10848.

Wen–Chung Shieh et al., "A simple asymmetric synthesis of 4–arylphenylalanines via palladium–catalysed cross–coupling reaction of arylboronic acids with tyrosine triflate" *Journal of Organic Chemistry*, vol. 57, No. 1, Jan. 1992, pp. 379–381.

Stevenson Tetrahedron Letters 37 (46) 8375–8, 1996.*

Campbell Synthetic Communications 19 (13–14) 2265–72 Abstract Only, 1989.*

* cited by examiner

*Primary Examiner*—Robert Gerstl
(74) *Attorney, Agent, or Firm*—Arent Fox Kintner Plotkin & Kahn, PLLC

(57) ABSTRACT

A process for the preparation of heteroaryl-phenylalanines of formula (II) in which R is a hydrogen atom, a straight or branched $C_1$–$C_4$ alkyl groups or a benzyl group; $R_1$ is an optionally substituted 5 or 6 membered aromatic heterocyclic group with one or two heteroatoms selected among nitrogen, oxygen and sulphur; comprising a cross-coupling reaction among heteroaryl-zinc halide and phenylalanine derivatives is described. Compounds of formula (II) are intermediates useful for the preparation of compounds endowed with pharmacological activity.

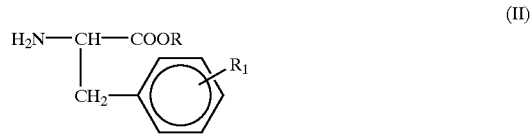

(II)

2 Claims, No Drawings

PROCESS FOR THE PREPARATION OF HETEROARYL-PHENYLALANINES

The present invention relates to a process for the preparation of heteroaryl-phenylalanines and, more particularly, it relates to a cross-coupling process for the preparation of phenylalanine derivatives having the phenyl group substituted by a heteroaryl group.

Heteroaryl-phenylalanines are known compounds, well described in the literature. For example, heteroaryl-phenylalanines endowed with pharmacological activity as antihypertensive agents have been described in the British patent n° 1554667 (Merck & Co., Inc.).

Moreover, heteroaryl-phenylalanines can be used as synthetic intermediates for the preparation of compounds endowed with pharmacological activity.

In the International patent application no. WO 97/24342 in the name of the same applicant, heteroaryl-phenylalanines are used for the preparation of N-mercaptoacyl derivatives of phenylalanine of formula

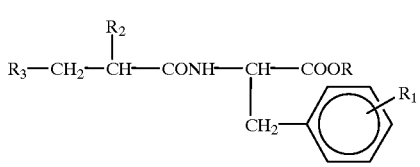

(I)

wherein

R is a hydrogen atom, a straight or branched $C_1$–$C_4$ alkyl group or a benzyl group;

$R_1$ is a 5 or 6 membered aromatic heterocyclic group, optionally substituted, having 1 or 2 heteroatoms selected among nitrogen, oxygen and sulphur;

$R_2$ is a $C_2$–$C_4$ straight or branched alkyl group or an aryl or arylalkyl group having from 1 to 6 carbon atoms in the alkyl moiety in which the aryl group is phenyl or a 5 or 6 membered aromatic heterocyclic group having 1 or 2 heteroatoms selected among nitrogen, oxygen and sulphur, optionally substituted by one or more substituents, the same or different, selected among halogen atoms, hydroxy groups, alkoxy, alkyl, alkylthio, alkylsulfonyl or alkoxycarbonyl groups having from 1 to 6 carbon atoms in the alkyl moiety, $C_1$–$C_3$ alkyl groups comprising one or more fluorine atoms, carboxy groups, nitro groups, amino or aminocarbonyl groups, acylamino groups, aminosulfonyl groups, mono- or di-alkylamino or mono- or di-alkylaminocarbonyl groups having from 1 to 6 carbon atoms in the alkyl moiety;

$R_3$ is a mercapto group or a $R_4$COS group convertible into a mercapto group in the body in which $R_4$ is a straight or branched $C_1$–$C_4$ alkyl group or a phenyl group.

Such compounds are endowed with metallopeptidases inhibitory activity and are useful in therapy for the treatment of cardiovascular diseases.

Many processes for the preparation of heteroaryl-phenylalanines are described in the literature.

Within this field, the processes comprising cross-coupling reactions starting from heterocyclic compounds and phenylalanine derivatives are particularly attractive.

For example, 4-(2-furanyl)-phenylalanine is prepared following a cross-coupling process comprising the reaction between N-(tert-butoxycarbonyl)-tyrosine triflate methyl ester and 2-furanboronic acid in the presence of palladium (0)tetrakis(triphenylphosphine) as described by W. C. Shieh in J. Org. Chem. 1992, 57, 379–381.

Nevertheless, as reported by the same Author, for the preparation of such a compound with valuable yield, amounts of catalyst equal to 30% in moles compared to 2-furanboronic acid, significantly higher than the ones requested for the conversion of other arylboronics substrates, i.e. phenylboronics, are needed.

An alternative route to the above process for the preparation of thienyl-phenylalanine, essentially comprising a cross-coupling reaction between thienylboronic acids and bromo-phenylalanine in the presence of palladium acetate and tri(o-tolyl)phosphine, has been described by M. J. Burk et al. in J. Am. Chem. Soc. 1994, 116, 10847–10848.

The arylboronic derivatives used as synthetic intermediates in the above processes are in turn prepared from the corresponding aryl-magnesium or aryl-lithium derivatives, by reaction with trialkylborates.

Nevertheless, to avoid the formation of di- or tri-arylboron derivatives as by-products, the preparation of the arylboronic acids, for example 2- and 3-furanboronic acids, requires reaction temperatures particularly low equal to −70° C. (J. Org. Chem. 1984, 49, 5237–5243).

According to an alternative synthetic process, the heteroaryl-phenylalanines can be prepared by cross-coupling between halogenated heterocyclic derivatives and stannyl-phenylalanine derivatives (Bioconjugate Chem., 1993, 4, 574–580); nevertheless the alkylstannanes used for the preparation of stannyl-phenylalanines are highly toxic compounds.

Therefore, the high toxicity and the prolonged and difficult preparation of some intermediates make the cross-coupling processes for the synthesis of heteroaryl-phenylalanine, described in the literature, unsuitable for industrial application.

Now we have found a process for the preparation of heteroaryl-phenylalanines by cross-coupling reaction that uses organo-zinc compounds, easily practicable and particularly indicated for an industrial application.

Therefore, object of the present invention is a process for the preparation of heteroaryl-phenylalanines of formula

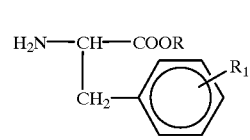

(II)

in which

R is a hydrogen atom, a straight or branched $C_1$–$C_4$ alkyl groups or a benzyl group;

$R_1$ is an optionally substituted 5 or 6 membered aromatic heterocyclic group with one or two heteroatoms selected among nitrogen, oxygen and sulphur;

that comprises the reaction between a compound of formula

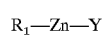

(III)

in which $R_1$ has the above reported meanings and Y is a chlorine, bromine or iodine atom; and a compound of formula

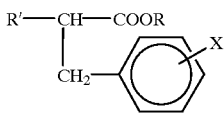

in which
R has the above reported meanings;
R' is an optionally protected amino group;
X is an iodine or bromine atom or a methansulfonyloxy, fluoromethansulfonyloxy, p.toluensulfonyloxy or trifluoromethansulfonyloxy group;
in the presence of a transition-metal (0) based catalyst;
and, when R' is a protected amino group, the deprotection reaction of the amino group.

The process object of the present invention is easily practicable and it enables to obtain the heteroaryl-phenylalanines of formula II with high yields, equal to or greater than 80% with respect to the starting compound of formula IV.

The cross-coupling reaction, according to the process object of the present invention, is carried out by reaction between an organo-zinc compound of formula III and a compound of formula IV.

Preferably, compound III and compound IV are used in a molar ratio III:IV from 1:1 to 3:1.

Still more preferably, the molar ratio of the compounds III:IV is from 1:1 to 2:1.

In the process object of the present invention the compounds of formula IV in which X is a iodine atom are preferably used.

The cross-coupling reaction is carried out in the presence of a transition-metal(0) based catalyst.

The amount of the catalyst is preferably from 0.05% to 5% in moles with respect to the organo-zinc compound of formula III.

Preferred examples of transition-metal(0) based catalysts are optionally supported palladium or nickel, in the presence of ligands such as, for example, triphenylphosphine.

The transition-metal(0) based catalysts can be optionally prepared in situ starting from the corresponding salts such as, for example, nickel chloride, cobalt chloride, nickel acetylacetonate, ferric chloride, palladium chloride, lithium tetrachlorocuprate, palladium acetate and palladium acetylacetonate.

Exclusively for practical reasons, palladium tetrakis(triphenylphosphine), nickel tetrakis(triphenylphosphine) or palladium on charcoal in the presence of triphenylphosphine, optionally prepared in situ as described, for example, in Org. Synth., 66, 67–74, 1988, are preferred.

The cross-coupling reaction is carried out in the presence of an organic solvent.

Suitable organic solvents are, for example, $C_6$–$C_{12}$ aliphatic hydrocarbons, tetrahydrofuran, di-ethyl ether, methyl-tert-butyl ether, ethylene glycol di-methyl ether, dioxane, toluene, xylene or mixtures thereof.

Preferably tetrahydrofuran, toluene or mixtures thereof are used.

Usually the reaction temperature is between 20° C. and the reflux temperature of the reaction mixture.

Preferably, a temperature between 40° C. and 60° C. is used.

From a practical point of view, the use of a compound of formula IV in which R' is a protected amino group is preferred for the preparation of the compounds of formula II.

Examples of suitable protecting groups are acetyl, benzyloxycarbonyl, tert-butoxycarbonyl, formyl, benzyl, ethoxycarbonyl and phthaloyl.

Preferably, the protective group is tert-butoxycarbonyl or formyl.

The starting compounds of formula IV in which R' is a protected amino group are known compounds or they are easily prepared according to known methods from the corresponding derivatives of formula IV in which R' is an amino group ($H_2N$—) (Bioconjugate Chem. 1993, 4, 574–580).

When R' is a protected amino group, the compounds of formula II according to the present process are prepared by cross-coupling reaction and subsequent deprotection of the amino group.

The deprotection is carried out according to standard procedures.

For a general reference on the use of protective groups in organic chemistry see Theodora W. Greene and Peter G. M. Wuts "Protective Groups in Organic Synthesis", John Wiley & Sons, Inc., II Ed., 1991.

Usually, the cross-coupling reaction is carried out starting from a compound of formula IV in which R is different from hydrogen, hence obtaining the corresponding compounds of formula II (R different from hydrogen). From these, by working according to conventional procedures, the corresponding compounds of formula II in which R=H can be obtained.

The starting compounds of formula III are known compounds or they are easily prepared according to known methods.

For example, the compounds of formula III can be prepared by reaction of the corresponding heteroaryl-lithium or heteroaryl-magnesium derivatives with an anhydrous zinc halide, e.g. zinc chloride, as likewise reported in Heterocycles, Vol. 31, No. 12, 1990, 2181–2186. Examples of compounds of formula II, that can be prepared according to the process object of the present invention, are the compounds in which the $R_1$ group is an aromatic heterocyclic group such as, for example, thiazole, isoxazole, oxazole, isothiazole, pyrazole, imidazole, thiophene, pyrrole, pyridine, pyrimidine, pyrazine, pyridazine and furan.

Specific examples of compounds of formula II are:
4-(2-thiazolyl)-phenylalanine;
4-(2-pyridyl)-phenylalanine;
4-(3-pyridyl)-phenylalanine;
4-(2-furyl)-phenylalanine;
4-(3-furyl)-phenylalanine;
4-(5-pyrimidinyl)-phenylalanine;
4-(2-pyrazinyl)-phenylalanine;
4-(2-thienyl)-phenylalanine;
4-(3-thienyl)-phenylalanine;
and the corresponding methyl and ethyl esters.

According to a particularly advantageous aspect of the process object of the present invention, the starting compounds of formula III are prepared in situ from the corresponding heteroaryl-lithium or heteroaryl-magnesium derivatives and hence directly used in the cross-coupling reaction.

More particularly, the heteroaryl-lithium or heteroaryl-magnesium derivatives are reacted with an anhydrous zinc halide, in the presence of the same solvent used for the cross-coupling reaction, to obtain the corresponding heteroaryl-zinc derivatives of formula III.

Therefore, the in situ so prepared compounds of formula III are reacted with the compounds of formula IV, according to the process object of the present invention.

The preparation of compounds of formula III is carried out using a molar ratio anhydrous zinc halide: heteroaryl-lithium or heteroaryl-magnesium derivative from 1:1 to 3:1.

Preferably, the heteroaryl-zinc derivatives of formula III are prepared with anhydrous zinc chloride.

The heteroaryl-lithium or heteroaryl-magnesium derivatives are known compounds or they are easily prepared according to known methods, as described, for example. in J. Am. Chem. Soc. 1952, 74, 6260–6262 or in the just mentioned Heterocycles, Vol. 31, No. 12, 1990, 2181–2186.

In a preferred embodiment of the process object of the present invention, the compounds of formula II are prepared starting from the corresponding heteroaryl-magnesium derivatives, by their reaction with an anhydrous zinc halide and subsequent cross-coupling reaction of the resultant compounds of formula III, in the same medium, as previously described.

The compounds of formula II can be used as synthetic intermediates for the preparation of compounds endowed with pharmacological activity such as, for example, the N-mercaptoacyl derivatives of phenylalanine of formula I, as disclosed in the just mentioned International patent application no. WO 97/24342.

In a particularly preferred embodiment, the process object of the present invention is used for the preparation of the compounds endowed with pharmacological action described in the aforesaid International patent application.

In a preferred embodiment of the process object of the present invention, a suitable amount of heteroaryl-magnesium halide is treated with an anhydrous zinc halide in a molar ratio respectively equal to 1:2, at room temperature and in the presence of a suitable solvent.

Therefore the compound of formula IV, properly protected, is added to the reaction mixture containing the in situ so prepared compound of formula III.

The cross-coupling reaction is carried out in the presence of catalytic amounts, for example equal to 1% in moles, of an in situ prepared palladium based catalyst.

The compounds of formula II, in the protected form, are thus obtained, in high yields, by heating the reaction mixture.

The subsequent deprotection reaction, carried out according to standard procedures, leads to the compounds of formula II.

The resultant compounds of formula II can be used as such, for example as synthetic intermediates for the preparation of pharmacologically active compounds.

The process object of the present invention is easily practicable and it enables to obtain the heteroaryl-phenylalanines of formula II with high yields and with mild reaction conditions.

Moreover, starting from a compound of formula IV as a single stereoisomer, the process object of thre present invention enables to obtain the compounds of formula II with a high optical purity, without any racemization.

Finally, the use of particularly stable intermediates, easily obtainable and usable in situ for the subsequent reactions without any further purification step, makes the process object of the present invention particularly suitable for the industrial application. With the aim to illustrate the present invention the following examples are now given.

EXAMPLE 1
Preparation of N-(tert-butoxycarbonyl)-4-(2-thiazolyl)-L-phenylalanine methyl ester A solution of 2-thiazolyl magnesium bromide, prepared starting from 2-bromo-thiazole (0.528 Kg; 3.22 moles) and magnesium turnings (0.093 Kg; 3.82 moles) in a 1:1 mixture of tetrahydrofuran:toluene (1.8 l), was slowly added in 2 hours to a suspension, prepared by slow adding anhydrous zinc chloride (0.853 Kg; 6.27 moles) in tetrahydrofuran (1.92 l ), under stirring and in an inert atmosphere at the temperature of 30° C.

The mixture was heated at 50° C. and N-(tert-butoxycarbonyl)-4-iodo-L-phenylalanine methyl ester (1.0 Kg; 2.34 moles) was gradually added.

A previously prepared mixture of palladium acetate (8 g, 0.036 moles) and triphenylphosphine (19.2 g; 0.072 moles) was added to the resultant mixture.

The mixture, kept under stirring at the temperature of 50° C. for 2 hours up to completion of the reaction (TLC hexane: ethyl acetate=7:3), was then cooled at room temperature and poured into an ice and water (3 Kg) bath containing toluene (1 l)

At that time glacial acetic acid (130 g) was added and the phases were separated. The aqueous phase was extracted with toluene (0.5 l) and the combined organic phases were washed twice with water (2.2 l) and evaporated to dryness under vacuum affording N-(tert-butoxycarbonyl)-4-(2-thiazolyl)-L-phenylalanine methyl ester (1.19 Kg), used as such in the subsequent reaction.

EXAMPLE 2
Preparation of N-(tert-butoxycarbonyl)-4-(2-thiazolyl)-D,L-phenylalanine methyl ester A solution of 2-thiazolyl magnesium bromide prepared by 2-bromo-thiazole (1.8 g; 11 mmoles) and magnesium turnings (320 mg; 13.1 mmoles) in a 1:1 mixture of tetrahydrofuran:toluene (6.6 ml) was gradually added in 0.5 hours to a suspension, prepared by gradually adding anhydrous zinc chloride (3 g; 22 mmoles) to tetrahydrofuran (6.6 ml), kept under stirring and under inert atmosphere at 30° C.

Then, the mixture was heated to 50° C. and N-tert-butoxycarbonyl)-4-bromo-D,L-phenylalanine methyl ester (1.6 g; 4.5 mmoles) was added.

Palladium acetate (33.6 mg; 0.15 mmoles) and triphenylphosphine (118 mg, 0.45 mmoles) were added to the resultant mixture.

The mixture, kept under stirring at 50° C. for 15 hours, was then cooled up to room temperature and poured into an ice and water bath (10 ml) containing toluene (10 ml).

Then, glacial acetic acid (about 1 g) was added and the phases were separated. The organic phase was evaporated to dryness.

The residue consisted of about 70% of N-(tert-butoxycarbonyl)-4-(2-thiazolyl)-D,L-phenylalanine methyl ester and of about 15% of starting compound (TLC eluent hexane:ethylacetate=6:4).

EXAMPLE 3
Preparation of N-formyl-4-(2-thiazolyl)-L-phenylalanine methyl ester By working in a way similar to that described in example 1 but starting from N-formyl-4-iodo-L-phenylalanine methyl ester, N-formyl-4-(2-thiazolyl)-L-phenylalanine methyl ester was obtained (yield > 90%) as a crude to be used as such without any further purification.

EXAMPLE 4
Preparation of 4-(2-thiazolyl)-L-phenylalanine methyl ester dihydrochloride Thionyl chloride (0.48 Kg; 4.03 moles) was added dropwise, in 1.5 hours, to a solution of N-(tert-butoxycarbonyl)-4-(2-thiazolyl)-L-phenylalanine methyl ester (1.208 Kg; 2.06 moles), prepared as described in example 1, in methanol (1.6 l), kept under stirring, under inert atmosphere and at a temperature of 15° C.

At the end of the addition, the suspension was allowed to warm to 25° C. and kept under stirring for 1 hour.

Methylethylketone (3.4 l) was then added to the resultant mixture and, by heating to reflux, the mixture of solvents (1.9 l) was distilled.

The resultant suspension was cooled to 20° C. and the formed precipitate was filtered and washed with methylethylketone (3×0.3 l) yielding, after drying under vacuum, 4-(2-thiazolyl)-L-phenylalanine methyl ester dihydrochloride [820 g; 91.5% yield calculated on N-(tert-butoxycarbonyl)-4-iodo-L-phenylalanine methyl ester described in example 1; HPLC titre 87%].

What is claimed is:

1. A method for preparing of heteroaryl-phenylalanines of the formula:

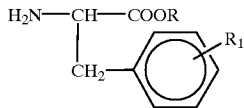
(II)

in which
R is a hydrogen atom, a $C_1$–$C_4$ straight or branched alkyl group or a benzyl group;
$R_1$ is an optionally substituted 5 or 6 membered aromatic heterocyclic group with one or two heteroatoms selected among nitrogen, oxygen or sulfur; comprising:
reacting a compound of the formula:

(III)

in which
$R_1$ has the above meaning and Y is a chlorine, bromine or iodine atom with the following compound:

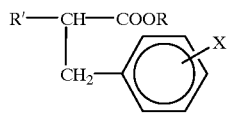
(IV)

in which
R has the above reported meaning;
R' is an optionally protected amino group;
X is an iodine or bromine atom or a methylsulfonyloxy, fluoromethansulfonyloxy, para toluenesulfonyloxy or a trifluoromethanesulfonyloxy group, in the presence of 1.0% to 3.5% by moles of a transition-metal (0) based catalyst with respect to the organo-zinc compound of formula III;
and, when R' is a protected amino group, conducting a deprotection reaction of the amino group.

2. A process for preparing N-mercaptoacyl derivatives of phenylalanine of the formula:

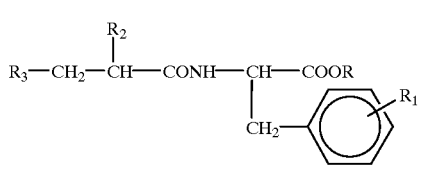
(I)

in which
R is a hydrogen atom, a $C_1$–$C_4$ straight or branched alkyl group or a benzyl group; and $R_1$ is an optionally substituted 5 or 6 membered aromatic heterocyclic group with one or two heteroatoms selected from nitrogen, oxygen or sulfur;
$R_2$ is a $C_2$–$C_4$ straight or branched alkyl group or an aryl or arylalkyl group having from 1 to 6 carbon atoms in the alkyl moiety in which the aryl group is a phenyl or a 5 or 6 membered aromatic heterocyclic group with 1 or 2 heteroatoms selected from nitrogen, oxygen, or sulfur and optionally substituted with one or more like or different substituents selected from halogen atoms, hydroxy groups, alkoxy, alkyl, alkythio, alkylsulfonyl or alkoxycarbonyl groups having from 1 to 6 carbon atoms in the alkyl moiety, $C_1$–$C_3$ alkyl groups having one or more fluorine atoms, carboxyl groups, nitro groups, amino or amino carbonyl groups, acylamino groups, aminosulfonyl groups, mono- or di-alkylamino or mono- or di-alkylaminocarbonyl groups having from 1 to 6 carbon atoms in the alkyl moiety;
$R_3$ is a mercapto group or a $R_4$ COS group capable of convertion in the body into a mercapto group in which $R_4$ is a $C_1$–$C_4$ straight or branched alkyl group or a phenyl group, said method comprising:
reacting a compound of the formula:

(III)

with the following compound:

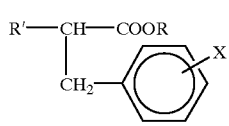
(IV)

in which R and R' are as above defined;
X is an iodine or bromine atom or methylsulfonyloxy, flouromethansulfonyloxy, para toluenesulfonyloxy or a trifluoromethanesulfonyloxy group, in the presence of 1.0% to 3.5% by moles of a transition-metal (0) based catalyst with respect to the organo-zinc compound formula III;
Y is a chlorine, bromine or iodine atom, in the presence of a transition-metal (0) based catalyst, and when R' is a protected amino group, conducting a deprotecting reaction of the amino group to obtain a compound of formula:

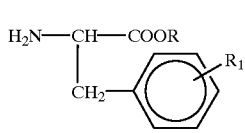
(II)

in which R and $R_1$ are as above defined.

* * * * *